United States Patent
Hamanaka et al.

(10) Patent No.: US 10,888,253 B2
(45) Date of Patent: Jan. 12, 2021

(54) AUDIOMETER

(71) Applicant: RION Co., Ltd., Tokyo (JP)

(72) Inventors: Ryoichi Hamanaka, Tokyo (JP); Kaori Sato, Tokyo (JP)

(73) Assignee: RION Co., Ltd., Tokyo (JP)

( * ) Notice: Subject to any disclaimer, the term of this patent is extended or adjusted under 35 U.S.C. 154(b) by 0 days.

(21) Appl. No.: 16/330,073

(22) PCT Filed: Oct. 4, 2017

(86) PCT No.: PCT/JP2017/036143
§ 371 (c)(1),
(2) Date: Mar. 1, 2019

(87) PCT Pub. No.: WO2018/070320
PCT Pub. Date: Apr. 19, 2018

(65) Prior Publication Data
US 2019/0209053 A1     Jul. 11, 2019

(30) Foreign Application Priority Data

Oct. 14, 2016     (JP) .................................. 2016-203063

(51) Int. Cl.
*A61B 5/12*        (2006.01)
*H04R 1/10*       (2006.01)
(Continued)

(52) U.S. Cl.
CPC .............. *A61B 5/121* (2013.01); *A61B 5/002* (2013.01); *A61B 5/123* (2013.01); *G16H 50/20* (2018.01);
(Continued)

(58) Field of Classification Search
CPC ........... A61B 5/121; A61B 5/12; A61B 5/123; A61B 5/0002; A61B 2560/0214;
(Continued)

(56) References Cited

U.S. PATENT DOCUMENTS 3,949,735 A  *  4/1976  Klar ......................... A61B 5/12
                                                              600/559
4,964,304 A     10/1990  Eckstein
(Continued)

FOREIGN PATENT DOCUMENTS

JP     H06501625 A     2/1994
JP     2009160373 A    7/2009
(Continued)

OTHER PUBLICATIONS

International Search Report dated Dec. 19, 2017 filed in PCT/JP2017/036143.
(Continued)

*Primary Examiner* — Nimeshkumar D Patel
*Assistant Examiner* — Nashmiya S Fayyaz
(74) *Attorney, Agent, or Firm* — Rankin, Hill & Clark LLP (57) ABSTRACT

An audiometer is provided which has: a main body section; and multiple sets of a headphone section and a response operation section, wherein the main body section performs wireless communication with the headphone section and performs wireless communication with the response operation section independently of the wireless communication with the headphone section, thereby supplying a test sound output command to the headphone section to cause the headphone section to output the test sound and receiving information on operation by a subject from the response operation section, and performs the wireless communication with the headphone section and the response operation section of each set by a time-division multiplexing system.

8 Claims, 4 Drawing Sheets

(51) Int. Cl.
*G16H 50/20* (2018.01)
*A61B 5/00* (2006.01)
*H04B 7/26* (2006.01)

(52) U.S. Cl.
CPC .... *H04R 1/1008* (2013.01); *A61B 2560/0209* (2013.01); *A61B 2560/0214* (2013.01); *H04B 7/2643* (2013.01)

(58) Field of Classification Search
CPC .......... A61B 2560/0209; H04R 1/1008; G16H 50/20; H04B 7/2643
USPC .......................................................... 73/585
See application file for complete search history.

(56) References Cited

U.S. PATENT DOCUMENTS

| | | | |
|---|---|---|---|
| 5,197,332 A | 3/1993 | Shennib | |
| 9,407,982 B2* | 8/2016 | Donaldson | H04R 1/1083 |
| 2004/0052237 A1* | 3/2004 | Schiff | H04L 1/0006 |
| | | | 370/345 |
| 2004/0185821 A1* | 9/2004 | Yuasa | H04W 52/0277 |
| | | | 455/343.5 |
| 2007/0204694 A1* | 9/2007 | Davis | A61B 5/121 |
| | | | 73/585 |
| 2007/0204695 A1* | 9/2007 | Gross | A61B 5/121 |
| | | | 73/585 |
| 2007/0232255 A1* | 10/2007 | Masuda | H04B 1/385 |
| | | | 455/343.1 |
| 2009/0060287 A1 | 3/2009 | Hyde | |
| 2009/0062686 A1 | 3/2009 | Hyde | |
| 2014/0205109 A1* | 7/2014 | Theiler | H04R 1/1083 |
| | | | 381/74 |
| 2016/0241947 A1* | 8/2016 | Degraye | H04R 3/12 |
| 2018/0167715 A1* | 6/2018 | Graylin | G10K 11/17827 |

FOREIGN PATENT DOCUMENTS

| | | |
|---|---|---|
| JP | 2009171544 A | 7/2009 |
| WO | 2008110016 A1 | 9/2008 |

OTHER PUBLICATIONS

Decision to Grant dated Mar. 16, 2017 for the corresponding Japanese Patent Application No. 2016-203063.

* cited by examiner

AUDIOMETER

TECHNICAL FIELD

The present invention relates to an audiometer.

BACKGROUND ART

A certain audiometry apparatus includes a base unit and a remote unit (see, e.g., Patent Literature 1).

This base unit includes an audiometer, an FM signal transmitter, and an FM signal receiver. The audiometer is configured to generate an audiometric test signal (an audible signal). The FM signal transmitter is configured to transmit the audiometry signal to the remote unit. At this point, the FM signal transmitter modulates a frequency having any of two channels with the audiometric test signal. Thus, the audiometric test signal is transmitted by the FM signal transmitter. Subsequently, the FM signal receiver receives a test result signal from the remote unit.

The remote unit includes right and left earphones, a handpad, a receiver, and an transmitter. The receiver is configured to receive the above-described audiometric test signal to supply the received audiometric test signal to one of the right and left earphones corresponding to the above-described channel. The transmitter is configured to transmit, to the base unit, the test result signal corresponding to operation of the handpad by a patient.

Further, according to the above-described audiometry apparatus, the remote unit can be provided to each of multiple patients to simultaneously perform tests for the multiple patients. At this point, the audiometry apparatus assigns, by a frequency-division multiplexing system, two channels to each remote unit, thereby performing communication among the base unit and multiple remote units.

CITATION LIST

Patent Literature

PATENT LITERATURE 1: JP-T-6-501625

SUMMARY OF THE INVENTION

Problems Solved by the Invention

However, in the above-described apparatus, two channels of frequency bands are necessary for a single subject. Thus, in the case of performing audiometry for multiple subjects, a wide frequency band is necessary. Thus, cross talk (interference) with existing wireless equipment easily occurs. For this reason, depending on a usage situation of surrounding wireless communication, it is difficult to smoothly perform the audiometry.

Generally, in this device, bands without the need of a license (a band of 2.4 GHz, a band of 920 MHz, and the like) are used. Thus, in a case where a wide frequency band is necessary for the audiometry, cross talk (interference) with existing wireless equipment such as a wireless local area network (LAN) easily occurs, and therefore, it is difficult to avoid such cross talk (interference).

An audiometer of the present disclosure has been made in view of the above-described problems. That is, an object of the present disclosure is to provide an audiometer configured so that cross talk (interference) with existing wireless equipment can be easily avoided and therefore audiometry for multiple subjects can be smoothly performed.

Solution to the Problems

An audiometer according to an embodiment of the present disclosure includes multiple sets of a headphone section and a response operation section and a main body section. The main body section performs wireless communication with the headphone sections, and performs wireless communication with the response operation sections independently of the wireless communication with the headphone sections. That is, the main body section supplies, via the wireless communication, a test sound output command to the headphone sections to cause the headphone sections to output the test sound. In addition, the main body section receives information on operation by subjects from the response operation sections. At this point, the main body section performs the wireless communication with the headphone section and the response operation section of each set by a time-division multiplexing system.

Moreover, an audiometer according to an embodiment of the present disclosure includes multiple sets of a headphone section and a response operation section. The response operation section and the headphone section included in each set perform wireless communication with each other using a specific time slot different from those of other sets among a predetermined number of time slots included in a single frame in the time-division multiplexing system. By such wireless communication, the headphone section outputs test sound to a subject. Moreover, the headphone section receives information on operation by the subject from the corresponding response operation section.

Effects of the Invention

According to the audiometer of the present disclosure, cross talk (interference) with the existing wireless equipment can be easily avoided. Thus, the audiometry for the multiple subjects can be smoothly performed.

DESCRIPTION OF THE EMBODIMENTS

Hereinafter, embodiments of the present disclosure will be described with reference to the drawings.

First Embodiment

Figure 1:
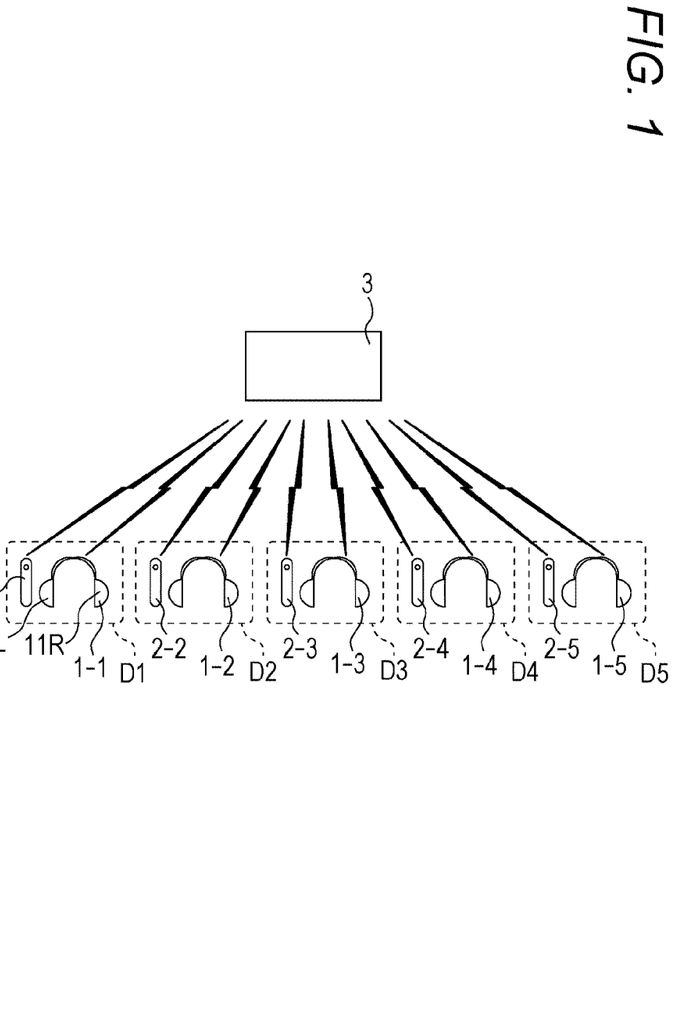
FIG. 1 is a view of a configuration of an audiometer according to a first embodiment of the present disclosure.

FIG. 1 is a view of a configuration of an audiometer according to a first embodiment of the present disclosure. The audiometer illustrated in FIG. 1 includes multiple headphone sections 1-1 to 1-5 (in this case, five headphone sections), multiple response operation sections 2-1 to 2-5 (in this case, five response operation sections), and a main body section 3. A single measurement device set Di including a pair of headphone section 1-i and response operation section 2-i (i=1, . . . , 5) is assigned to a single subject. The headphone section 1-i is configured to output test sound to the subject to which the headphone section 1-i is assigned. The response operation section 2-i is operated by the subject to which the response operation section 2-i is assigned when the subject hears the test sound.

The headphone sections 1-1 to 1-5 and the main body section 3 are not connected to each other via cables and are physically separated from each other, the response operation sections 2-1 to 2-5 and the main body section 3 are not connected to each other via cables and are physically separated from each other, and the headphone sections 1-1 to 1-5 and the response operation sections 2-1 to 2-5 are not connected to each other via cables and are physically separated from each other. The headphone sections 1-1 to 1-5 and the main body section 3 are connected to each other via wireless communication, and the response operation sections 2-1 to 2-5 and the main body section 3 are connected to each other via wireless communication. Thus, the headphone sections 1-1 to 1-5, the response operation sections 2-1 to 2-5, and the main body section 3 each include independent power sources. The headphone sections 1-1 to 1-5 and the response operation sections 2-1 to 2-5 can use, without being connected to a power cable, batteries as the power sources to perform audiometry.

The main body section 3 is configured to perform the wireless communication with the headphone sections 1-1 to 1-5 by a time-division multiplexing system and perform, independently of such wireless communication, the wireless communication with the response operation sections 2-1 to 2-5 by the time-division multiplexing system. That is, the main body section 3 supplies, via the wireless communication, a test sound output command to the headphone sections 1-1 to 1-5, thereby causing the headphone sections 1-1 to 1-5 to output the test sound. In addition, the main body section 3 receives, via the wireless communication, operation information from the response operation sections 2-1 to 2-5.

Specifically, the test sound output command is transmitted from the main body section 3 to all of the headphone sections 1-1 to 1-5 using specific time slots of a predetermined number of time slots in a single frame. Moreover, the operation information on the response operation sections 2-1 to 2-5 is sequentially transmitted from the response operation sections 2-1 to 2-5 to the main body section 3 at multiple other specific time slots than the above-described specific time slots of all time slots.

Note that in the present embodiment, the test sound output command is a digital signal. For example, amplitude shift keying (ASK) or phase shift keying (PSK) is, as necessary, used as a modulation method for the wireless communication. Moreover, e.g., a frequency band of 920 MHz is used for the wireless communication. According to the test sound output command, a sound pressure level, a test sound frequency, and the like are specified for the test sound for a left earphone section 11L and/or a right earphone section 11R.

The headphone sections 1-1 to 1-5 generate test sound signals specified by the test sound output command, thereby outputting the test sound according to the test sound signals. As described above, in the headphone sections 1-1 to 1-5, the test sound signals (audio signals) are generated. Thus, noise due to the wireless communication is less superimposed on the test sound signals.

Figure 2:
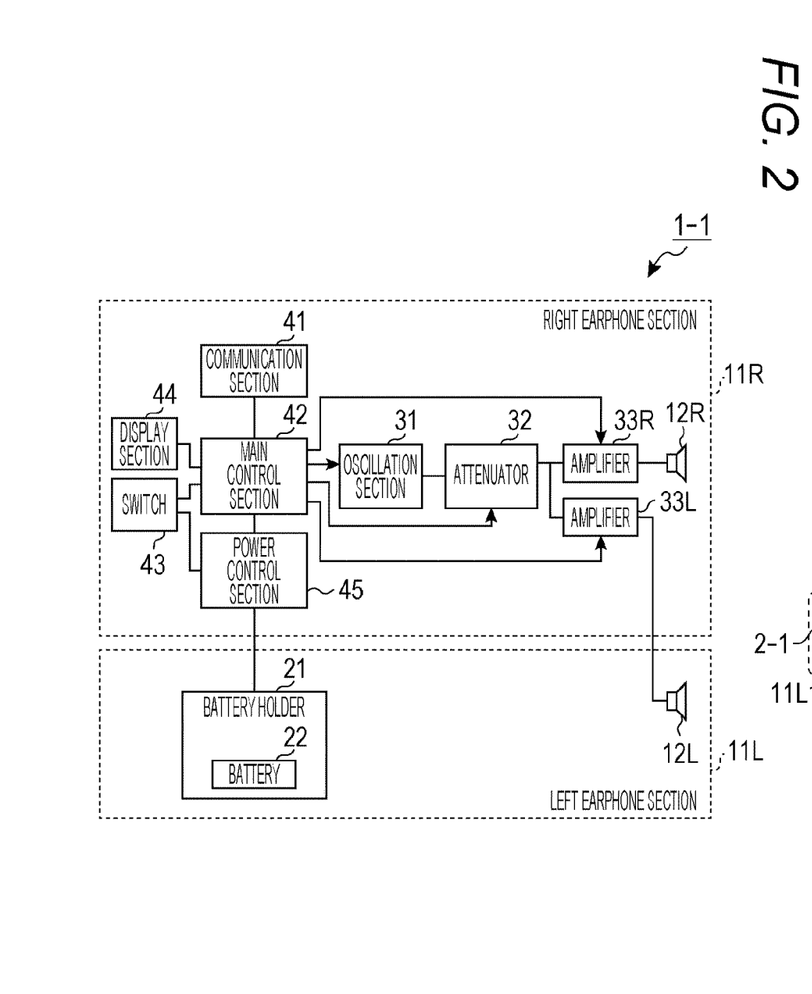
FIG. 2 is a block diagram of a configuration of a headphone section 1-1 of FIG. 1.

FIG. 2 is a block diagram of a configuration of the headphone section 1-1 of FIG. 1. As illustrated in FIG. 2, the headphone section 1-1 includes the left earphone section 11L in a left housing, the right earphone section 11R in a right housing, and a headband connecting the left housing and the right housing to each other.

The left earphone section 11L includes a speaker 12L. The speaker 12L is configured to output the test sound to the left ear of the subject. The right earphone section 11R includes a speaker 12R. The speaker 12R is configured to output the test sound to the right ear of the subject.

Further, in the present embodiment, the left earphone section 11L further includes a battery holder 21. A battery 22 (a primary battery or a secondary battery) is inserted into the battery holder 21.

Moreover, in the present embodiment, the right earphone section 11R further includes an oscillation section 31, an attenuator 32, an amplifier 33L for the left speaker 12L, and an amplifier 33R for the right speaker 12R.

The oscillation section 31 is a circuit configured to oscillate a signal having a frequency specified by a control signal and output the oscillated signal as the test sound signal. The attenuator 32 is a circuit configured to decrease, at an attenuation rate specified by the control signal, the amplitude of the test sound signal output by the oscillation section 31. Each of the amplifier 33L and the amplifier 33R is a circuit configured to increase, at an amplification rate specified by the control signal, the amplitude of the test sound signal output by the oscillation section 31.

Further, in the present embodiment, the right earphone section 11R includes a communication section 41, a main control section 42, a switch 43, a display section 44, and a power control section 45.

The communication section 41 includes a communication circuit, an antenna, and the like. The communication section 41 is configured to execute the above-described wireless communication to receive the test sound output command and supply the test sound output command to the main control section 42. In addition, the communication section 41 is configured to transmit voltage information and output sound information on the headphone section 1-1, these types of information being supplied from the main control section 42. The output sound information described herein includes, for example, the level and frequency of sound output from the earphone sections 11L and 11R, tested ear (left or right), intermittence or continuation of test sound output, a test sound ON or OFF condition (i.e., an ON or OFF condition of a sound presentation switch of the main body section 3) according to the test sound output command, a noise setting (noise output or noise intermission), and the presence or absence of communication error detection.

The main control section 42 is configured to supply the control signal corresponding to the test sound output command to the oscillation section 31, the attenuator 32, and the amplifiers 33L, 33R. In this manner, the main control section 42 outputs, to the speaker 12L and/or the speaker 12R, the test sound signal specified by the test sound output command (the test sound signal with the specified frequency and sound pressure level). Then, the main control section 42 causes the speaker 12L and/or the speaker 12R to output the test sound. Note that in the case of supplying the test sound signal from the amplifier 33L to the speaker 12L, the test sound signal is supplied from the amplifier 33L to the speaker 12L via a signal cable arranged through the headband. Note that the main control section 42 is implemented by a microcomputer or a digital signal processor, for example.

The switch 43 is a switch configured to receive operation for activating the headphone section 1-1. The display section 44 is an indicator configured to display, e.g., an operation mode of the headphone section 1-1.

The power control section 45 is electrically connected to the battery holder 21 (i.e., the battery 22) via the headband. The power control section 45 is configured to switch the operation mode of the headphone section 1-1 according to, e.g., operation for the switch 43 and the state of the communication, thereby selecting the operation mode. Further, the power control section 45 is configured to supply power from the battery 22 to an internal circuit (e.g., the communication section 41, the main control section 42, and the display section 44) corresponding to the currently-selected operation mode.

Note that the power control section 45 measures the voltage of the battery 22 to supply voltage information indicating the measured voltage to the main control section 42. The main control section 42 supplies such voltage information to the communication section 41.

As described above, the headphone section 1-1 is operated with the power from the battery 22 as the power source. Then, the headphone section 1-1 measures the power-source voltage of the power source (the battery 22). The voltage information indicating the measured power-source voltage of the headphone section 1-1 is repeatedly transmitted by the headphone section 1-1 as a cycle including a predetermined number of frames at a single specific time slot of a single time frame.

In the present embodiment, the battery holder 21 and the battery 22 are arranged at the left earphone section 11L. Note that the battery holder 21 and the battery 22 may be arranged at the right earphone section 11R. Moreover, in the present embodiment, the oscillation section 31, the attenuator 32, the amplifiers 33L, 33R, the communication section 41, the main control section 42, the switch 43, the display section 44, and the power control section 45 are arranged at the right earphone section 11R. Note that some or all of these components may be arranged at the left earphone section 11L.

Note that the remaining headphone sections 1-2 to 1-5 also have configurations similar to that of the headphone section 1-1.

Figure 3:
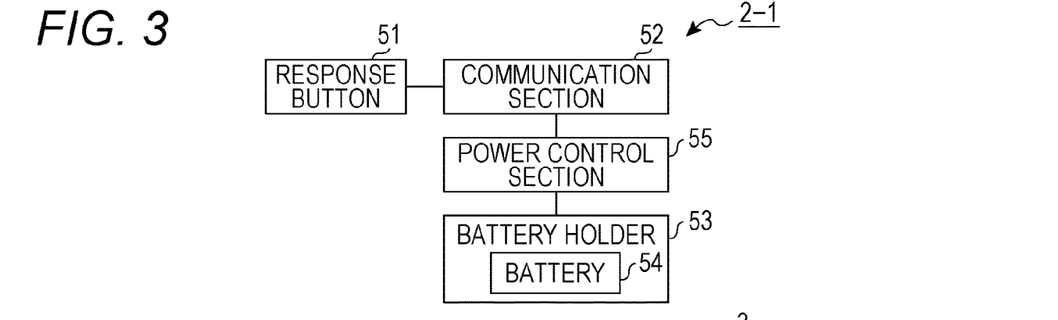
FIG. 3 is a block diagram of a configuration of a response operation section 2-1 of FIG. 1.

FIG. 3 is a block diagram of a configuration of the response operation section 2-1 of FIG. 1. As illustrated in FIG. 3, the response operation section 2-1 includes a response button 51 operated by the subject, a communication section 52, a battery holder 53 (and a battery 54 as a primary or secondary battery inserted into the battery holder 53), and a power control section 55.

For example, the response button 51 is a push button switch to be brought into an ON condition only while the switch is pressed.

The communication section 52 includes a communication circuit, an antenna, and the like. The communication section 52 is configured to execute the above-described wireless communication to transmit operation information indicating the presence or absence of operation for the response button 51 and voltage information supplied from the power control section 55.

The power control section 55 is electrically connected to the battery holder 53 (i.e., the battery 54). The power control section 55 is configured to switch an operation mode of the response operation section 2-1 according to, e.g., operation for the response button 51 and the state of the communication, thereby selecting the operation mode. Further, the power control section 55 is configured to supply power from the battery 54 to an internal circuit (e.g., the communication section 52) corresponding to the currently-selected operation mode.

Note that the power control section 55 measures the voltage of the battery 54 to supply the voltage information indicating the measured voltage to the communication section 52.

As described above, the response operation section 2-1 is operated with the power from the battery 54 as the power source, thereby measuring the power-source voltage of the power source (the battery 54) of the response operation section 2-1. Then, the response operation section 2-1 uses the communication section 52 to repeatedly transmit, together with the operation information, the voltage information indicating the measured power-source voltage in a predetermined cycle (in this case, a cycle including two frames).

For example, the communication section 52 of the response operation section 2-1 determines, at multiple predetermined time points in a single frame, whether or not the response button 51 is pressed. Then, based on a determination result (e.g., the number of determinations or the rate of determination as the response button 51 being pressed), the communication section 52 identifies an operation state of the response button 51 as "pressed" or "not pressed." The identified operation information with a value corresponding to "pressed" or "not pressed" is transmitted by the communication section 52 at the transmission timing of predetermined cycle (in this case, a cycle including two frames). That is, even when the operation state is any of "pressed" or "not pressed," the operation state is constantly transmitted in every predetermined cycle.

Note that the remaining response operation sections 2-2 to 2-5 also have configurations similar to that of the response operation section 2-1.

Figures 4, 5:
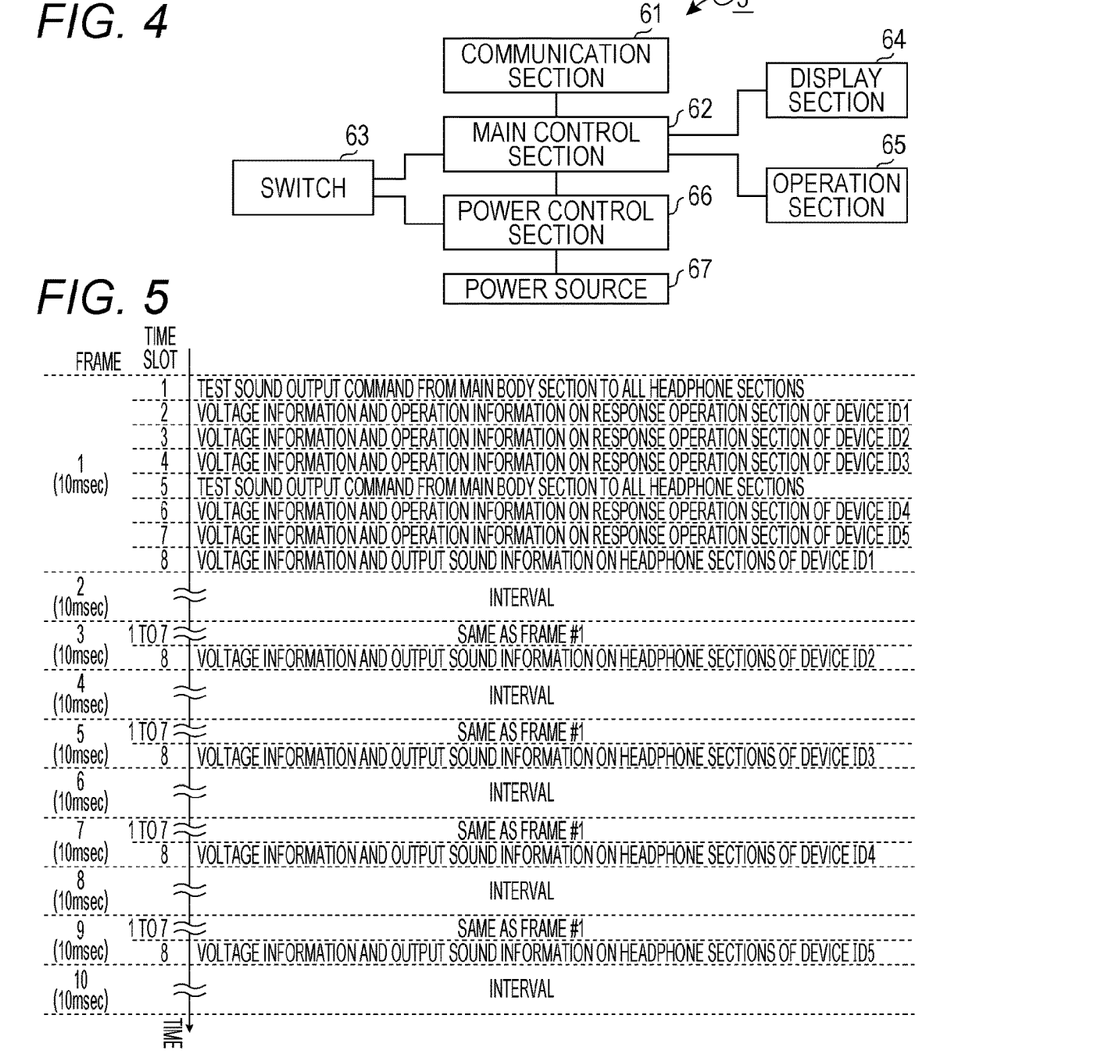
FIG. 4 is a block diagram of a configuration of a main body section 3 of FIG. 1.
FIG. 5 is a chart of one example of time slot assignment in time-division multiplexing communication between a main body section 3 and each of headphone sections 1-1 to 1-5 and each of response operation sections 2-1 to 2-5 in the first embodiment.

FIG. 4 is a block diagram of a configuration of the main body section 3 of FIG. 1. As illustrated in FIG. 4, the main body section 3 includes a communication section 61, a main control section 62, a switch 63, a display section 64, an operation section 65, a power control section 66, and a power source 67.

The communication section 61 includes a communication circuit, an antenna, and the like. The communication section 61 is configured to execute the above-described wireless communication to transmit the above-described test sound output command and receive the above-described operation information and the above-described voltage information.

The main control section 62 uses the communication section 61 to transmit the test sound output command to the headphone sections 1-1 to 1-5 included in multiple measurement device sets D1 to D5. Then, the main control section 62 receives the operation information from the response operation sections 2-1 to 2-5. Accordingly, the audiometry for multiple subjects is executed. Moreover, the main control section 62 uses the communication section 61 to remotely monitor the power-source voltages of the headphone sections 1-1 to 1-5 and the response operation sections 2-1 to 2-5 based on the voltage information transmitted therefrom. Then, the main control section 62 displays these power-source voltages on the display section 64. In addition, the main control section 62 informs, when the headphone section **1-*i* or the response operation section 2-*i* having a power-source voltage of equal to or lower than a predetermined value is detected, an operator of such detection. Note that the main control section 62** is implemented by, for example, a microcomputer or a digital signal processor.

Specifically, the main body section 3 repeatedly receives, together with the operation information, the voltage information on the response operation sections 2-1 to 2-5 as a cycle including two frames. Then, based on such voltage information, the main body section 3 monitors the power-source voltages of the response operation sections 2-1 to 2-5. Moreover, the main body section 3 sequentially receives the voltage information on the headphone sections 1-1 to 1-5, using specific time slots, and repeating in a cycle of a predetermined number of frames. Then, based on the voltage information, the main body section 3 monitors the power-source voltages of the headphone sections 1-1 to 1-5.

The switch 63 is a switch to be operated by the operator to activate the main body section 3.

The display section 64 is, for example, an indicator or a liquid crystal display. The display section 64 is configured to display the progress and result (e.g., an audiogram) of the audiometry and the power-source voltages of the headphone sections 1-1 to 1-5 and the response operation sections 2-1 to 2-5. The operation section 65 is configured to receive operation of the operator by, e.g., a hard key. The main control section 62 causes the communication section 61 to transmit the test sound output command according to operation of the operator received by the operation section 65. In addition, the main control section 62 causes the display section 64 to display, e.g., the operation information and the voltage information received by the communication section 61.

The power control section 66 is electrically connected to the power source 67. The power control section 66 is configured to switch an operation mode of the main body section 3 according to, e.g., operation for the switch 63 and the state of the communication, thereby selecting the operation mode. Further, the main control section 62 supplies power from the power source 67 to an internal circuit (e.g., the communication section 61, the main control section 62, and the display section 64) corresponding to the currently-selected operation mode. The power source 67 is a battery or a power circuit configured to generate DC power from an AC commercial power source.

First wireless communication and second wireless communication between the main body section 3 and each of the headphone sections 1-1 to 1-5 and the response operation sections 2-1 to 2-5 will be described herein in detail.

FIG. 5 is a chart of one example of time slot assignment regarding time-division multiplex communication between the main body section 3 and each of the headphone sections 1-1 to 1-5 and the response operation sections 2-1 to 2-5 in the first embodiment.

For example, as illustrated in FIG. 5, a single frame is divided into eight time slots #1 to #8. Moreover, 10 frames are included in a single cycle. The time length of a single frame is determined such that the upper limit (in this case, five) of the number of measurement device sets Di, delay time until the test sound is output from all headphone sections 1-1 to 1-5 after the operator has operated the main body section 3, delay time until operation of the response operation sections 2-1 to 2-5 by the subject is detected at the main body section 3 after such operation has been performed by the subject, and the like are equal to or less than predetermined values, and such that the audiometry can be properly executed according to standards, for example, JIS standard. The time length of a single frame is herein set to 10 milliseconds.

In the present embodiment, device IDs 1 to 5 are each assigned to the measurement device sets D1 to D5. The main body section 3 identifies and controls the measurement device sets D1 to D5 by the device IDs 1 to 5.

First, in a frame #1, (a) the time slot #1 is assigned to transmission of the test sound output command from the main body section 3 to the headphone sections 1-1 to 1-5 of all measurement device sets D1 to D5; (b) the time slot #2 is assigned to transmission of the above-described voltage information and the above-described operation information from the response operation section 2-1 of the device ID1, i.e., the measurement device set D1, to the main body section 3; (c) the time slot #3 is assigned to transmission of the above-described voltage information and the above-described operation information from the response operation section 2-2 of the device ID2, i.e., the measurement device set D2, to the main body section 3; and (d) the time slot #4 is assigned to transmission of the above-described voltage information and the above-described operation information from the response operation section 2-3 of the device ID3, i.e., the measurement device set D3, to the main body section 3.

Further, in the frame #1, (e) the time slot #5 is assigned to transmission of the test sound output command from the main body section 3 to the headphone sections 1-1 to 1-5 of all measurement device sets D1 to D5; (0 the time slot #6 is assigned to transmission of the above-described voltage information and the above-described operation information from the response operation section 2-4 of the device ID4, i.e., the measurement device set D4, to the main body section 3; (g) the time slot #7 is assigned to transmission of the above-described voltage information and the above-described operation information from the response operation section 2-5 of the device ID5, i.e., the measurement device set D5, to the main body section 3; and (h) the time slot #8 is assigned to transmission of the above-described voltage information and the above-described output sound information from the headphone section 1-1 of the device ID1, i.e., the measurement device set D1, to the main body section 3.

Frames #2, #4, #6, #8, #10 are intervals. These intervals are utilized for, e.g., detection of an additional measurement device set. That is, the wireless communication between the main body section 3 and each of the headphone sections 1-1 to 1-5 and the response operation sections 2-1 to 2-5 is executed in every other frame. That is, a single frame of an internal (a communication stop period) is provided between a frame in which certain wireless communication is performed and a frame in which subsequent wireless communication is performed.

Next, the same time slots #1 to #7 as those of the frame #1 are assigned to a frame #3. Note that a time slot #8 of the frame #3 is assigned to transmission of the above-described voltage information and the above-described output sound information from the headphone section 1-2 of the device ID 2, i.e., the measurement device set D2, to the main body section 3.

Moreover, the same time slots #1 to #7 as those of the frame #1 are assigned to a frame #5. Note that a time slot #8 of the frame #5 is assigned to transmission of the above-described voltage information and the above-described output sound information from the headphone section 1-3 of the device ID3, i.e., the measurement device set D3, to the main body section 3.

Further, the same time slots #1 to #7 as those of the frame #1 are assigned to a frame #7. Note that a time slot #8 of the frame #7 is assigned to transmission of the above-described voltage information and the above-described output sound information from the headphone section 1-4 of the device ID4, i.e., the measurement device set D4, to the main body section 3.

In addition, the same time slots #1 to #7 as those of the frame #1 are assigned to a frame #9. Note that a time slot #8 of the frame #9 is assigned to transmission of the above-described voltage information and the above-described output sound information from the headphone section 1-5 of the device ID5, i.e., the measurement device set D5, to the main body section 3.

As described above, transmission of the test sound output command from the main body section 3 to the headphone sections 1-1 to 1-5 of all measurement device sets D1 to D5 and transmission of the above-described voltage information and the above-described operation information from the response operation sections 2-1 to 2-5 of the device ID1 to ID5, i.e., the measurement device sets D1 to D5, to the main body section 3 are executed in every other frame. On the other hand, transmission of the above-described voltage information and the above-described output sound information from the headphone sections 1-1 to 1-5 of the device ID1 to ID5, i.e., the measurement device sets D1 to D5, to the main body section 3 is executed in the cycle including 10 frames.

Each headphone section 1-*i* (i=1, . . . , 5) and each response operation section 2-*i* (i=1, . . . , 5) identify the time slots regarding these sections themselves (the above-described time slots at which the command and the information as described above need to be received or transmitted) based on the device ID assigned to the measurement device set Di to which these sections themselves belong. The main body section 3 identifies the device having transmitted the above-described information, i.e., the headphone section 1-*i* or the response operation section 2-*i*, using a specific time slot based on the device ID assigned to the measurement device set Di to which the headphone section 1-*i* or the response operation section 2-*i* belongs.

Note that by, e.g., transmission of a synchronous signal to the beginning of the frame by the main body section 3 and reception of the synchronous signal by the headphone sections 1-1 to 1-5 and the response operation sections 2-1 to 2-5, frame synchronization is made among the main body section 3, the headphone sections 1-1 to 1-5, and the response operation sections 2-1 to 2-5. By dividing such a frame cycle, the timing of each time slot is accurately identified at each of the main body section 3, the headphone sections 1-1 to 1-5, and the response operation sections 2-1 to 2-5. Note that the synchronous signal may contain a frame number. Alternatively, a signal indicating the start of the frame cycle may be inserted into the beginning of the leading frame #1 as a cycle (hereinafter referred to as a "frame cycle") including a predetermined number of frames (in this case, 10 frames), and in this manner, the frame cycle may be synchronized. In this manner, each of the headphone sections 1-1 to 1-5 can identify the time slot of the frame in which, e.g., the voltage information on this section itself needs to be transmitted.

Note that in the present embodiment, the number of all measurement device sets (D1 to D5) is five, and the number of time slots in a single frame is eight. Note that these numbers are not specifically limited.

The operation modes of the headphone sections 1-1 to 1-5, the response operation sections 2-1 to 2-5, and the main body section 3 will be described herein in detail.

Figure 6:
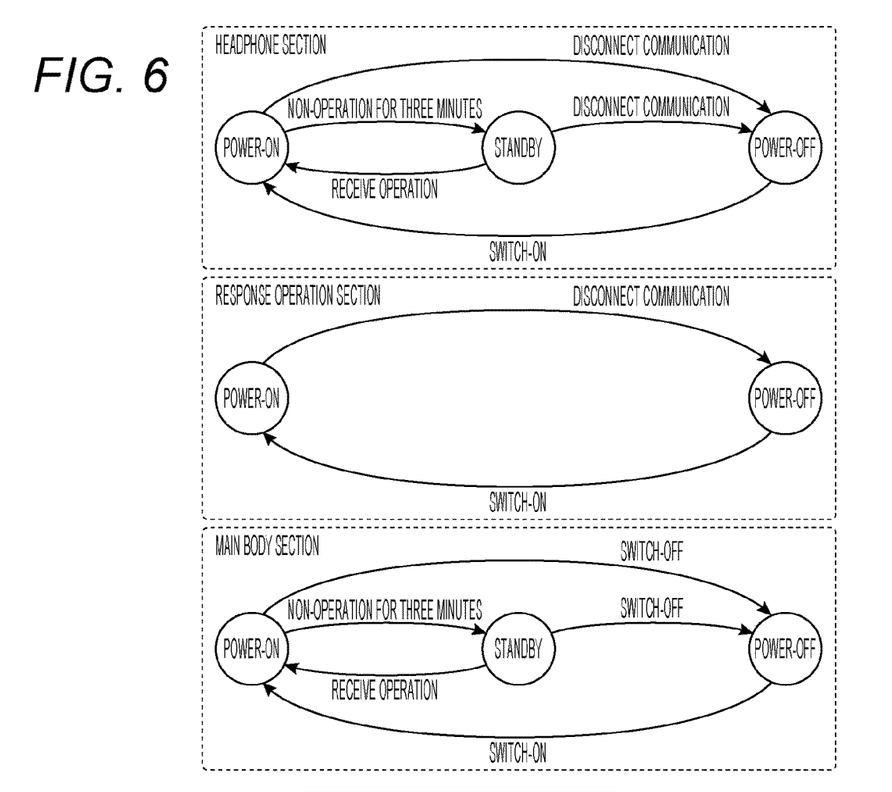
FIG. 6 is a diagram of state transition of power modes of the headphone sections 1-1 to 1-5, the response operation sections 2-1 to 2-5, and the main body section 3 of FIG. 1.

FIG. 6 is a diagram of state transition of power modes of the headphone sections 1-1 to 1-5, the response operation sections 2-1 to 2-5, and the main body section 3 of FIG. 1.

As illustrated in FIG. 6, the headphone section 1-*i* (i=1, . . . , 5) has, as the operation modes, power-ON, standby, and power-OFF. The response operation section 2-*i* (i=1, . . . , 5) has, as the operation modes, power-ON and power-OFF. The main body section 3 has, as the operation modes, power-ON, standby, and power-OFF.

For example, in the power-ON mode, various display sections can be lighted up. In the standby mode, various display sections are lighted off. As described above, the audiometer of the present embodiment is configured such that power consumption in the standby mode is lower than power consumption in the power-ON mode. Note that in any of the power-ON mode and the standby mode, the first wireless communication and the second wireless communication as described above are executed. In the power-OFF mode, all types of power supply are stopped. Note that in the case of requiring power for detection of operation (switch-ON) for activation, power supply for such detection is performed.

As illustrated in FIG. 6, the headphone section 1-*i* (a) changes to the power-ON mode when the switch 43 (FIG. 2) is pressed in the power-OFF mode; (b) automatically changes to the standby mode when a non-operation period (a period for which a operation section, not shown in this FIG. 6, is not operated) of a predetermined length (in this case, three minutes) is detected in the power-ON mode; (c) automatically returns to the power-ON mode when operation is detected in the standby mode; and (d) automatically changes to the power-OFF mode when communication with the main body section 3 is stopped for predetermined time (in this case, three minutes) in the power-ON mode or the standby mode.

Moreover, as illustrated in FIG. 6, the response operation section 2-*i* (a) changes to the power-ON mode when a switch (not shown) is pressed in the power-OFF mode; and (b) automatically changes to the power-OFF mode when communication with the main body section 3 is stopped for predetermined time (in this case, three minutes) in the power-ON mode.

Further, as illustrated in FIG. 6, the main body section 3 (a) changes to the power-ON mode when the switch 63 (FIG. 4) is pressed in the power-OFF mode; (b) automatically changes to the standby mode when a non-operation period (a period for which the operation section 65 is not operated) of a predetermined length (in this case, three minutes) is detected in the power-ON mode; (c) automatically returns to the power-ON mode when operation is detected in the standby mode; and (d) automatically changes to the power-OFF mode when switch-OFF (e.g., re-pressing of the switch 63) is detected in the power-ON mode or the standby mode. When the main body section 3 is brought into the power-OFF mode, communication between the main body section 3 and each of the headphone sections 1-1 to 1-5 and the response operation sections 2-1 to 2-5 is stopped. Thus, in this case, the headphone sections 1-1 to 1-5 and the response operation sections 2-1 to 2-5 autonomously changes to the power-OFF mode after a lapse of predetermined time.

Next, operation of the audiometer according to the first embodiment will be described.

First, the main body section 3 detects the measurement device sets D1 to D5 present in a wireless communication area. For example, the audiometer of the present embodiment can be configured such that according to transmission of a searching signal by the main control section 62 via the communication section 61, the device having received the searching signal, i.e., the headphone section 1-*i* or the response operation section 2-*i*, transmits a response signal including the set Di corresponding to the device ID of the device itself. In this manner, the communication section 61 receives the response signal, so that the measurement device set Di present in the wireless communication area can be identified based on the set Di corresponding to the device ID of the response signal.

Note that in, e.g., the case illustrated in FIG. 5, the main body section 3 can use up to five measurement device sets D1 to D5 to perform the audiometry. Alternatively, the main body section 3 may use the measurement device sets Di less than the upper limit (in this case, five) to perform the audiometry. In this case, when an additional measurement device set Dj is detected at the above-described interval, the main body section 3 adds the additional measurement device set Dj to the audiometry.

Then, the main body section 3 transmits, using specific time slots (the above-described time slots #1, #5), the test sound output command specified by operation for the operation section 65 by the operator or the test sound output command determined according to an automatic audiometry program to the headphone sections 1-1 to 1-5 included in the detected measurement device sets D1 to D5. When receiving the test sound output command, the headphone sections 1-1 to 1-5 generate the test sound signals (the audio signals) specified by the test sound output command, and output the test sound from the speaker 12L and/or the speaker 12R based on the test sound signals.

Meanwhile, the response operation sections 2-1 to 2-5 each monitor whether or not the subjects press the response buttons 51. In addition, each of the response operation sections 2-1 to 2-5 measures the voltage of the battery 54. Further, each of the response operation sections 2-1 to 2-5 transmits the operation information and the voltage information when the time slot assigned to this section itself arrives. The main body section 3 receives the operation information and the voltage information using the time slot assigned to each response operation section 2-*i*.

The main body section 3 displays or records the presence or absence of operation by the subject based on the received operation information. Moreover, the main body section 3 monitors the power-source voltage of each response operation section 2-*i* based on the received voltage information to display the power-source voltage. When such a power-source voltage reaches equal to or lower than the predetermined value, the main body section 3 informs the operator of such a state.

Moreover, the headphone sections 1-1 to 1-5 each regularly transmit the voltage information and the output sound information using different time slots. The main body section 3 receives these types of information. Then, the main body section 3 monitors the power-source voltage of each headphone section 1-*i* based on the received voltage information to display such a power-source voltage. In a case where the power-source voltage reaches equal to or lower than the predetermined value or the test sound output command and the output sound information are not coincident with each other, each of the headphone sections 1-1 to 1-5 informs the operator of such a state.

As described above, the audiometer according to the first embodiment includes the pair of headphone section 1-*i* and response operation section 2-*i* included in each of the multiple sets Di (i=1, . . . , 5) and the main body section 3. The main body section 3 performs the first wireless communication with the headphone section 1-*i* by the time-division multiplexing system. In addition, the main body section 3 performs, independently of the first wireless communication, the second wireless communication with the response operation section 2-*i* by the time-division multiplexing system. That is, the main body section 3 supplies the test sound output command to the headphone section 1-*i*, thereby causing such a headphone section to output the test sound. In addition, the main body section 3 receives the operation information of the response operation section 2-*i* by the subject from the response operation section 2-*i*.

With this configuration, the wireless communication between the pair of headphone section 1-*i* and response operation section 2-*i* included in each of the multiple sets Di and the main body section 3 can be executed with a single frequency. Thus, cross talk (interference) with existing wireless equipment can be easily avoided. As a result, the audiometry for multiple subjects can be smoothly performed.

Second Embodiment

An audiometer according to a second embodiment of the present disclosure is configured so that headphone sections 1-1 to 1-5, response operation sections 2-1 to 2-5, and a main body section 3 can select a frequency to be used for wireless communication by the above-described time-division multiplexing system from multiple predetermined frequencies (channels). For example, a frequency specified by operator's operation or setting data is selected.

Note that other configurations and other types of operation of the audiometer according to the second embodiment are the same as those of the audiometer of the first embodiment.

Figure 7:
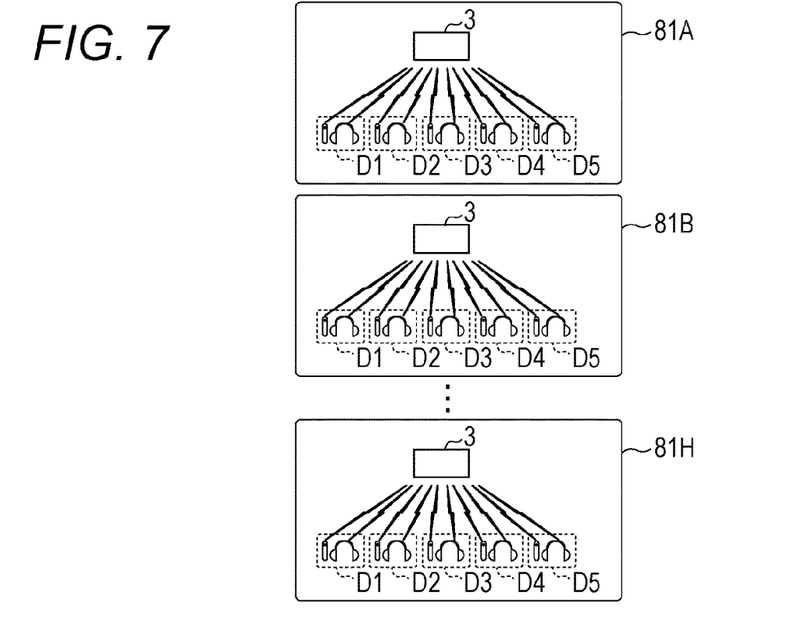
FIG. 7 is a view for describing a case where multiple audiometers are close to each other in a second embodiment.

FIG. 7 is a view for describing a case where multiple audiometers in the second embodiment are close to each other. For example, as illustrated in FIG. 7, in a case where multiple audiometers 81A, 81B, . . . , 81H are close to each other, when these audiometers use the same channel for the wireless communication, interference occurs. For this reason, each of the audiometers 81A, 81B, . . . , 81H uses, for the wireless communication, a specified channel different from those for other audiometers.

A group ID is assigned to each of the audiometers 81A, 81B, . . . , 81H. When the channel is set, the group ID and one or more channel IDs indicating a frequency to be used by multiple measurement device sets and a main body section included in the audiometer corresponding to the group ID are associated with each other. Channel IDs with different frequencies are each associated with different group IDs. Thus, the wireless communication is not interfered among the audiometers 81A, 81B, . . . , 81H.

For example, a headphone section 1-*i*, a response operation section 2-*i*, and a main body section 3 assigned to each audiometer (81A to 81H) may select a channel different from those of other audiometers from multiple preset channels according to operation by an operator and the like and may share such a channel. With this configuration, the frequency to be used for the above-described wireless communication can be changed such that the wireless communication is not interfered among the audiometers 81A, 81B, . . . , 81H.

For example, in a case where eight audiometers 81A to 81H each corresponding to eight group IDs can use 24 channels #1 to #24, e.g., three channels are assigned in advance to the audiometer corresponding to each group ID. Specifically, the channels #1, #9, #17 are assigned to the audiometer 81A corresponding to a group ID #1. The channels #2, #10, #18 are assigned to the audiometer 81B corresponding to a group ID #2. The channels #3, #11, #19 are assigned to the audiometer 81C corresponding to a group ID #3. The channels are similarly assigned to the audiometers 81D to 81H each corresponding to group IDs #4 to #8.

The channels are set as described above, so that proximity of the center frequencies of the channels among different audiometers can be prevented. Moreover, the main body section 3 of the audiometer corresponding to each group ID can select one of three channels having the best communication state.

The settings of the group ID are used as described above, so that multiple channels can be set for different audiometers. As a result, even in a case where the multiple audiometers are close to each other, cross talk (interference) with an audiometer having a different group ID or with existing wireless equipment can be easily avoided. Thus, audiometry for multiple subjects can be smoothly performed.

Third Embodiment

Figure 8:
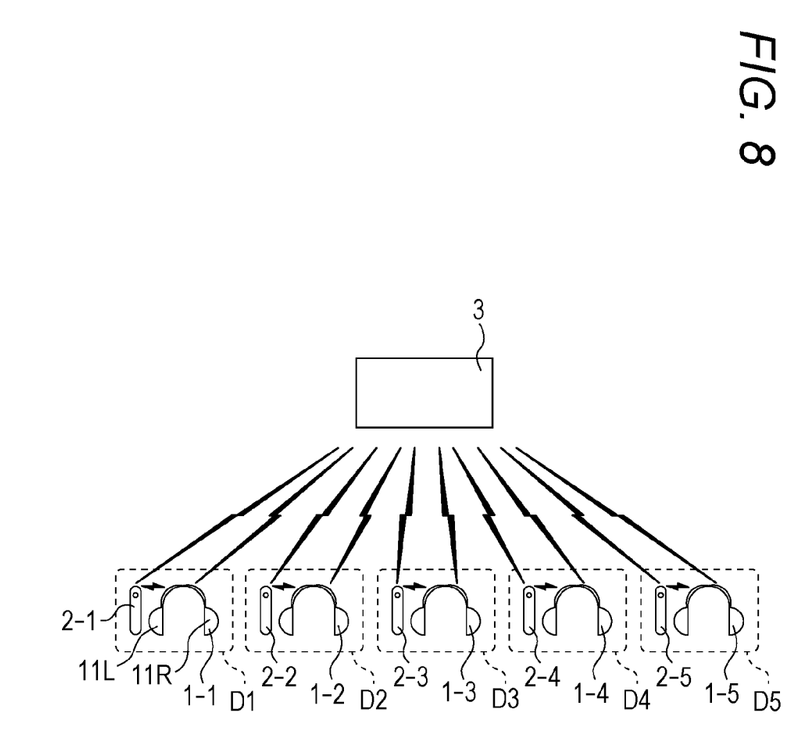
FIG. 8 is a view of a configuration of an audiometer according to a third embodiment of the present disclosure.

FIG. 8 is a view of a configuration of an audiometer according to a third embodiment of the present disclosure. Note that basic configuration and operation of a device assigned to the audiometer according to the third embodiment, i.e., headphone sections 1-1 to 1-5, response operation sections 2-1 to 2-5, and a main body section 3, are the same as those of the audiometers of the first and second embodiments, except for the following points.

In the third embodiment, wireless communication by a time-division multiplexing system similar to those of the first and second embodiments is executed. Note that in the first and second embodiments, the operation information and the voltage information transmitted by the response operation sections 2-1 to 2-5 are received by the main body section 3. However, in the third embodiment, operation information and voltage information transmitted by each of the response operation sections 2-1 to 2-5 are not received by the main body section 3, but are received by a corresponding one of the headphone sections 1-1 to 1-5.

That is, the operation information and the voltage information transmitted by the response operation section 2-1 are received by the corresponding headphone section 1-1, for example. Such operation information and such voltage information are not received by any of the main body section 3 and other headphone sections 1-2 to 1-5.

Thus, a response operation section 2-$i$ and a headphone section 1-$i$ of each of multiple sets Di (i=1, ..., 5) perform the wireless communication with each other using a specific time slot different from those of other sets among a predetermined number of time slots included in a single frame in the time-division multiplexing system. Then, each headphone section 1-$i$ outputs test sound to a subject via such wireless communication, and receives the information on operation by the subject from the corresponding response operation section 2-$i$.

For example, in the frames #1, #3, #5, #7, #9 in a case where the time slots are assigned as illustrated in FIG. 5, (a) the operation information is transmitted from the response operation section 2-1 of the measurement device set D1 to the headphone section 1-1 at the time slot #2; (b) the operation information is transmitted from the response operation section 2-2 of the measurement device set D2 to the headphone section 1-2 at the time slot #3; (c) the operation information is transmitted from the response operation section 2-3 of the measurement device set D3 to the headphone section 1-3 at the time slot #4; (d) the operation information is transmitted from the response operation section 2-4 of the measurement device set D4 to the headphone section 1-4 at the time slot #6; and (e) the operation information is transmitted from the response operation section 2-5 of the measurement device set D5 to the headphone section 1-5 at the time slot #7.

In the third embodiment, (a) the main body section 3 performs the wireless communication with the headphone sections 1-1 to 1-5 to transmit a test start command to the headphone sections; and then, (b) the main body section 3 receives, after completion of audiometry using the measurement device sets D1 to D5, a test result from the headphone sections 1-1 to 1-5.

When receiving the test start command, each headphone section 1-$i$ (i=1, ..., 5) sequentially outputs multiple types of test sound according to an automatic audiometry program. Then, each headphone section 1-$i$ (i=1, ..., 5) identifies the test result based on the operation information received from the corresponding response operation section 2-$i$. After completion of the audiometry, each headphone section 1-$i$ transmits the identified test result to the main body section 3.

For example, automatic audiometry such as an automatic threshold test or an automatic screening test is performed according to the automatic audiometry program. In the automatic threshold test, pure sound with various frequencies is output at various intensities (sound pressure levels). Then, measurement on whether or not the subject hears such pure tone is performed. That is, the automatic threshold test is a testing method for automatically checking an audible threshold for each frequency. In the automatic screening test, e.g., a test sound of 30 dB at 1 kHz and a test sound of 40 dB at 4 kHz are each output to the right and left ears. Then, measurement on whether or not the subject hears such test sound is performed. In this testing method, when the subject can hear the pure sound or the test sound, it is automatically determined as no abnormality being found. When the subject cannot hear the pure sound or the test sound, it is automatically determined as abnormality being found.

For example, before execution of the wireless communication by the above-described time-division multiplexing system, the main body section 3 may transmit the test start command to some or all of the headphone sections 1-1 to 1-5. Then, the main body section 3 may execute the wireless communication by the above-described time-division multiplexing system, thereby causing some or all of the headphone sections 1-1 to 1-5 to perform the audiometry. Alternatively, the main body section 3 may change a wireless communication method from the above-described time-division multiplexing system after having received audiometry completion information on the measurement device sets D1 to D5, the audiometry completion information being transmitted using a specific time slot (e.g., the above-described time slot #8) by the headphone sections 1-1 to 1-5. In this case, test results of the headphone sections 1-1 to 1-5 are received by the main body section 3 from some or all of the headphone sections 1-1 to 1-5. Note that in a case where no test start command is transmitted to the headphone section 1-$i$, the audiometry according to the first embodiment can be performed by a measurement device set Di simultaneously with audiometry by other measurement device sets Dj (j=1, . . . , 5 where i≠j).

Alternatively, the main body section 3 may transmit the test start command to all headphone sections 1-1 to 1-5 using specific time slots (e.g., the above-described times lots #1, #4), and thereafter, may sequentially receive the test results from the headphone sections 1-1 to 1-5 using a specific time slot (e.g., the above-describe time slot #8), for example.

Note that in the third embodiment, the audiometer may be, as same in the first and second embodiments, configured such that frame synchronization is made among the main body section 3, the headphone sections 1-1 to 1-5 and the response operation sections 2-1 to 2-5, by transmission of a synchronous signal to the beginning of the frame by the main body section 3 and reception of the synchronous signal by the headphone sections 1-1 to 1-5 and the response operation sections 2-1 to 2-5. Alternatively, instead of the main body section 3, a specific headphone section 1-$i$ may transmit the synchronous signal.

As described above, according to the third embodiment, the response operation section 2-$i$ and the headphone section 1-$i$ in each of the multiple sets Di (i=1, . . . , 5) perform the wireless communication with each other using a specific time slot different from those of other sets among the predetermined number of time slots included in a single frame in the time-division multiplexing system. Then, each headphone section 1-$i$ (i=1, . . . , 5) outputs the test sound to the subject by such wireless communication, and receives the information on operation by the subject from the corresponding response operation section 2-$i$.

With this configuration, the wireless communication among the headphone section 1-$i$ and the response operation section 2-$i$ in each of the multiple sets Di can be executed with a single frequency. Thus, as in the first embodiment, cross talk (interference) with existing wireless equipment can be easily avoided. As a result, the audiometry for multiple subjects can be smoothly performed.

Moreover, according to the third embodiment, the headphone section 1-$i$ (i=1, . . . , 5) of each of the multiple sets D1 to D5 can autonomously perform the audiometry in a manner matching to audibility of the subject according to the automatic audiometry program independently of other headphone sections 1-$j$ (i≠j). Thus, the audiometry for a subject group including subjects with a difference in audibility can be quickly performed.

Note that it is obvious for those skilled in the art that various changes and modifications can be made to the above-described embodiments. That is, such changes and modifications can be made without departing from the gist of the present embodiments and weakening intended advantageous effects. That is, the present disclosure is intended to include such changed and modified embodiments in the scope of the present embodiments.

The audiometer of the present disclosure may be the following first to eighth audiometers.

The first audiometer includes multiple sets of a headphone section and a response operation section; and a main body section configured to perform wireless communication with the headphone section and perform wireless communication with the response operation section independently of the wireless communication with the headphone section, thereby supplying a test sound output command to the headphone section to cause the headphone section to output the test sound and receiving information on operation by a subject on the response operation section. The main body section performs the wireless communication with the headphone sections and the response operation sections of the multiple sets by a time-division multiplexing system.

The second audiometer may be the first audiometer in which the test sound output command is transmitted from the main body section to the headphone sections of all sets using a specific time slot of a predetermined number of time slots included in a single frame, and the operation information on the response operation sections of the multiple sets is sequentially transmitted from the response operation sections to the main body section using multiple specific time slots different from the specific time slot at which the test sound output command is transmitted among the predetermined number of time slots.

The third audiometer may be the first or second audiometer in which the response operation section is operated with power of a battery as a power source, the response operation section measures the power-source voltage of the power source for the response operation section, and repeatedly transmits, together with the operation information, first voltage information indicating the measured power-source voltage of the response operation section, and the main body section receives the first voltage information together with the operation information to monitor the power-source voltage of the response operation section.

The fourth audiometer may be any one of the first to third audiometers in which the headphone section is operated with power of a battery as a power source, the headphone section included in each set measures the power-source voltage of the power source for the headphone section, and sequentially and repeatedly transmits second voltage information indicating the measured power-source voltage of the headphone section as a cycle including a predetermined number of frames at a single specific time slot of a single frame, and the main body section sequentially and repeatedly receives the second voltage information on the headphone sections included in the multiple sets in the cycle including the predetermined number of frames using the specific time slot, thereby monitoring the power-source voltage of the headphone section.

The fifth audiometer may be any one of the first to fourth audiometers in which the headphone section generates a test sound signal specified by the test sound output command to output the test sound according to the test sound signal.

The sixth audiometer may be any one of the first to fifth audiometers in which the main body section changes, according to a communication status, a frequency to be used for the wireless communication by the time-division multiplexing system from multiple predetermined frequencies.

The seventh audiometer may be an audiometer including multiple sets of a headphone section and a response operation section. The response operation section and the headphone section included in each set may perform wireless communication with each other using a specific time slot different from those of other sets among a predetermined number of time slots included in a single frame in the time-division multiplexing system. The headphone section may output test sound to a subject, and may receive information on operation by the subject on the response operation section.

The eighth audiometer may be the seventh audiometer further including a main body section. The main body section may perform wireless communication with the headphone sections (a) to transmit a test start command to the headphone sections and (b) receive test results from the headphone sections. When receiving the test start command, the headphone sections may sequentially output, according to an automatic audiometry program, multiple types of test sound, identify the test results based on the operation information received from the response operation sections, and transmit the identified test results.

INDUSTRIAL APPLICABILITY

The present invention is, for example, applicable to an audiometer configured to perform audiometry for multiple subjects simultaneously.

LIST OF REFERENCE NUMERALS 1-1 to 1-5 Headphone section
2-1 to 2-5 Response operation section
3 Main body section

The invention claimed is:
1. An audiometer comprising:
a first measurement device assigned to a first subject and a second measurement device assigned to a second subject, the first measurement device comprising a first headphone means for outputting a test sound to the first subject and a first response operation means for transmitting operation information indicating a presence or absence of a response operation of the first response operation means by the first subject, the second measurement device comprising a second headphone means for outputting the test sound to the second subject and a second response operation means for transmitting operation information indicating a presence or absence of a response operation of the second response operation means by the second subject; and
a main body means for performing wireless communication with the first and second headphone means, performing wireless communication with the first and second response operation means independently of the wireless communication with the first and second headphone means, supplying a test sound output command to the first and second headphone means to cause the first and second headphone means to output the test sound, and receiving the operation information from the first and second response operation means, wherein
the main body means performs the wireless communication with the first and second headphone means and the first and second response operation means by a time-division multiplexing system,
the first response operation means is assigned with a first time slot in a frame for transmitting the operation information indicating the presence or absence of the response operation of the first response operation means,
the second response operation means is assigned with a second time slot in the frame for transmitting the operation information indicating the presence or absence of the response operation of the second response operation means, the second time slot being different from the first time slot,
the main body means receives the operation information from the first response operation means at the first time slot,
the main body means receives the operation information from the second response operation means at the second time slot,
each of the first and second response operation means is operated with power of a battery as a power source,
the first response operation means measures a power-source voltage of the power source for the first response operation means, and transmits, together with the operation information indicating the presence or absence of the response operation of the first response operation means, first voltage information indicating the measured power-source voltage of the first response operation means to the main body means at the first time slot,
the second response operation means measures a power-source voltage of the power source for the second response operation means, and transmits, together with the operation information indicating the presence or absence of the response operation of the second response operation means, second voltage information indicating the measured power-source voltage of the second response operation means to the main body means at the second time slot, and
the main body means receives the first voltage information together with the operation information from the first response operation means at the first time slot and receives the second voltage information together with the operation information from the second response operation means at the second time slot to monitor the power-source voltage of the each of the first and second response operation means.
2. The audiometer according to claim 1, wherein
the test sound output command is transmitted from the main body means to the first and second headphone means using a specific time slot of a predetermined number of time slots included in a single frame, the specific time slot being different from the first time slot and the second time slot.
3. The audiometer according to claim 1, wherein
each of the first and second headphone means is operated with power of a battery as a power source,
each of the first and second headphone means measures a power-source voltage of the power source for the each of the first and second headphone means, and sequentially transmits third voltage information indicating the measured power-source voltage of the each of the first and second headphone means, using a single specific time slot of a single frame, which is different from the first time slot and the second time slot, and repeating in a cycle of a predetermined number of frames, and
the main body means sequentially receives the third voltage information on the each of the first and second headphone means, using the specific time slot, and repeating in a cycle of the predetermined number of frames, thereby monitoring the power-source voltage of the each of the first and second headphone means.
4. The audiometer according to claim 1, wherein
at least one of the first and second headphone means comprises an oscillator for generating a test sound signal specified by the test sound output command to output the test sound according to the test sound signal.
5. The audiometer according to claim 1, wherein
the main body means changes, according to a communication status, a frequency to be used for the wireless communication by the time-division multiplexing system from multiple predetermined frequencies.
6. An audiometer comprising:
a first measurement device assigned to a first subject and a second measurement device assigned to a second subject, the first measurement device comprising a first headphone means for outputting a test sound to the first subject and a first response operation means for transmitting operation information indicating a presence or absence of a response operation of the first response operation means by the first subject, the second mea- surement device comprising a second headphone means for outputting the test sound to the second subject and a second response operation means for transmitting operation information indicating a presence or absence of a response operation of the second response operation means by the second subject, wherein the first response operation means and the first headphone means perform wireless communication with each other using a specific time slot different from those for wireless communication between the second response operation means and the second headphone means among a predetermined number of time slots included in a single frame in the time-division multiplexing system, the first and second headphone means receive the operation information from the first and second response operation means, respectively, the first response operation means is assigned with a first time slot in the frame for transmitting the operation information indicating the presence or absence of the response operation of the first response operation means, the second response operation means is assigned with a second time slot in the frame for transmitting the operation information indicating the presence or absence of the response operation of the second response operation means, the second time slot being different from the first time slot, the first headphone means receives the operation information from the first response operation means at the first time slot, identifies a test result based on the received operation information from the first response operation means and transmits the test result identified by the first headphone means, the second headphone means receives the operation information from the second response operation means at the second time slot, identifies a test result based on the received operation information from the second response operation means and transmits the test result identified by the second headphone means, the audiometer further comprising a main body means for performing wireless communication with the first and second headphone means (a) to transmit a test start command to the first and second headphone means and (b) receive the test result identified by the first headphone means and the test result identified by the second headphone means from the first and second headphone means, respectively, and when receiving the test start command, the first and second headphone means sequentially output, according to an automatic audiometry program, multiple types of test sound.

7. The audiometer according to claim 1, wherein each of the first response operation means and the second response operation means comprises a response button, and the response operation includes an operation of the response button.

8. The audiometer according to claim 6, wherein each of the first response operation means and the second response operation means comprises a response button, and the response operation includes an operation of the response button.

* * * * *